US012762692B2

(12) United States Patent
Mei et al.

(10) Patent No.: US 12,762,692 B2
(45) Date of Patent: Oct. 13, 2026

(54) 3D ANALYSIS WITH OPTICAL COHERENCE TOMOGRAPHY IMAGES

(71) Applicant: TOPCON CORPORATION, Tokyo (JP)

(72) Inventors: Song Mei, Franklin Park, NJ (US); Zaixing Mao, Edgewater, NJ (US); Xin Sui, Oakland, NJ (US); Zhenguo Wang, Ridgewood, NJ (US); Kinpui Chan, Ridgewood, NJ (US)

(73) Assignee: TOPCON CORPORATION, Tokyo (JP)

( * ) Notice: Subject to any disclaimer, the term of this patent is extended or adjusted under 35 U.S.C. 154(b) by 223 days.

(21) Appl. No.: 16/845,307

(22) Filed: Apr. 10, 2020

(65) Prior Publication Data

US 2021/0319551 A1 Oct. 14, 2021

(51) Int. Cl.

| | |
|---|---|
| ***G06T 7/00*** | (2017.01) |
| ***A61B 3/10*** | (2006.01) |
| ***G06T 5/70*** | (2024.01) |
| ***G06T 7/11*** | (2017.01) |

(52) U.S. Cl.

CPC ............ *G06T 7/0012* (2013.01); *A61B 3/102* (2013.01); *G06T 5/70* (2024.01); *G06T 7/11* (2017.01); *G06T 2207/10101* (2013.01); *G06T 2207/20108* (2013.01); *G06T 2207/30041* (2013.01); *G06T 2207/30101* (2013.01)

(58) Field of Classification Search

CPC .................. A61B 3/102; A61B 5/0066; G06T 2207/30041; G06T 2207/10101; G06T 7/11; G06T 2207/30101; G06T 7/12; G06T 2207/20221

See application file for complete search history.

(56) References Cited

U.S. PATENT DOCUMENTS 10,136,812 B2 * 11/2018 Yasuno .................... A61B 3/14
2009/0281420 A1 * 11/2009 Passmore ................ G06T 7/254 382/130
2012/0120368 A1 * 5/2012 Fujimora ............... A61B 3/102 382/131
2013/0039557 A1 * 2/2013 Wei ........................ G06V 10/75 382/131
2017/0206657 A1 * 7/2017 Nozato ................ G06V 10/993
2017/0294015 A1 * 10/2017 Wang .................... G06T 7/0012
2017/0316567 A1 * 11/2017 Kotoku ................... G06T 11/00

(Continued)

FOREIGN PATENT DOCUMENTS

WO WO-2022004492 A1 * 1/2022 ............ A61B 3/102

OTHER PUBLICATIONS

Bing Nan Li, Chee Kong Chui, Stephen Chang, S.H. Ong, Integrating spatial fuzzy clustering with level set methods for automated medical image segmentation, Computers in Biology and Medicine, vol. 41, Issue 1, (Year: 2011).*

(Continued)

*Primary Examiner* — Gandhi Thirugnanam
(74) *Attorney, Agent, or Firm* — McDonald Hopkins LLC

(57) ABSTRACT

A method for generating clinically valuable analyses and visualizations of 3D volumetric OCT data by combining a plurality of segmentation techniques of common OCT data in three dimensions following pre-processing techniques. Prior to segmentation, the data may be subject to a plurality of separately applied pre-processing techniques.

16 Claims, 8 Drawing Sheets

(56) References Cited

U.S. PATENT DOCUMENTS

| | | | | |
|---|---|---|---|---|
| 2018/0144471 | A1* | 5/2018 | Govindjee | A61B 5/7282 |
| 2018/0263490 | A1* | 9/2018 | Jia | G06T 7/12 |
| 2019/0046030 | A9* | 2/2019 | Jia | A61B 3/1241 |
| 2019/0286899 | A1* | 9/2019 | Wyle | G06V 30/127 |
| 2020/0167656 | A1* | 5/2020 | Trenholm | G01B 9/02091 |
| 2020/0279352 | A1* | 9/2020 | Mao | A61B 5/7203 |
| 2021/0082163 | A1* | 3/2021 | Mei | G06T 5/008 |

OTHER PUBLICATIONS

Maloca, P., Gyger, C. & Hasler, P.W. A pilot study to compartmentalize small melanocytic choroidal tumors and choroidal vessels with speckle-noise free 1050 nm swept source optical coherence tomography (OCT choroidal "tumoropsy"). Graefes Arch Clin Exp Ophthalmol 254, 1211-1219 (2016). (Year: 2016).*

Miao Zhang, Jie Wang, Alex D. Pechauer, Thomas S. Hwang, Simon S. Gao, Liang Liu, Li Liu, Steven T. Bailey, David J. Wilson, David Huang, and Yali Jia, "Advanced image processing for optical coherence tomographic angiography of macular diseases," Biomed. Opt. Express 6, 4661-4675 (2015) (Year: 2015).*

Nicole K. Scripsema,et al.; Optical Coherence Tomography Angiography Analysis of Perfused Peripapillary Capillaries in Primary Open-Angle Glaucoma and Normal-Tension Glaucoma. Invest. Ophthalmol. Vis. Sci. 2016;57(9):OCT611-OCT620. (Year: 2016).*

Extended European Search Report for International Application No. 20173442.3 dated Oct. 30, 2020.

Maloca, et al., "A pilot study to image the vascular network of small melanocytic choroidal tumors with speckle noise-free 1050-nm swept source optical coherence tomography (OCT choroidal angiography)", Graefe's Archive for Clinical and Experimental Opthalmology, Springer Verlag, DE, vol. 254, No. 6, Feb. 4, 2016, pp. 1201-1210, XP035791229, ISSN: 0721-832X, DOI: 10.007/S00417-015-3259-9.

Huihong, et al., "Automatic Segmentation and Visualization of Choroid in OCT with Knowledge Infused Deep Learning", arxiv.org, Cornell University Library, 201 Olin Library Cornell University Ithaca, NY 14853, Feb. 6, 2020, XP081597783, pp. 1-12.

Agrawal, et al., "Choroidal vascularity index as a measure of vascular status of the choroid: Measurements in healthy eyes from a population-based study", Scientific Reports, vol. 6, No. 21090, DOI:10.1038/srep21090, pp. 1-9, Feb. 12, 2016.

Agrawal, et al., "Influence of scanning area on choroidal vascularity index measurement using optical coherence tomography", Acta Ophthalmologica, doi: 10.1111/aos.13442, vol. 95, 2017, pp. e770-e775.

Mao, et al., "Deep learning based noise reduction method for automatic 3D segmentation of the anterior of lamina cribrosa in optical coherence tomography volumetric scans", Biomedical Optics Express, vol. 10, No. 11, Nov. 1, 2019, pp. 5832-5851.

Duan, et al., "Automated segmentation and characterization of choroidal vessels in high-penetration optical coherence tomography", Optics Express, vol. 21, No. 13, doi:10.1364/oe.21.015787, Jul. 1, 2013, pp. 15787-15808.

Zhang, et al., "Automated Segmentation of the Choroid from Clinical SD-OCT", IOVS, vol. 53, No. 12, Nov. 2012, pp. 7510-7519.

Paris, et al., "Local Laplacian Filters: Edge-aware Image Processing with a Laplacian Pyramid", ACM Transaction on Graphics, vol. 58, No. 3, Mar. 2015.

Sonoda, et al., "Choroidal Structure in Normal Eyes and After Photodynamic Therapy Determined by Binarization of Optical Coherence Tomographic Images", Multidisciplinary Ophthalmic Imaging, IOVS, vol. 55, No. 6, Jun. 2014, pp. 3893-3898.

Sonoda, et al., "Luminal and Stromal Areas of Choroid Determined by Binarization Method of Optical Coherence Tomographic Images", American Journal of Ophthalmology, vol. 159, No. 6, Jun. 2015, pp. 1124-1131.

Srinath, et al., "Automated Detection of Choroid Boundary and Vessels in Optical Coherence Tomography Images", 2014 36th Annual International Conference of the IEEE Engineering in Medicine and Biology Society, DOI: 10.1109/EMBC.2014.6943555, Nov. 6, 2014, pp. 166-169.

Zheng, et al., "Choroidal Thickness and Choroidal Vessel Density in Nonexudative Age-Related Macular Degeneration Using Swept-Source Optical Coherence Tomography Imaging", IOVS, vol. 57, No. 14, iovs.arvojournals.org j ISSN: 1552-5783, Nov. 2016, pp. 6256-6264.

Zhou, et al., "Attenuation correction assisted automatic segmentation for assessing choroidal thickness and vasculature with swept-source OCT", Biomedical Optics Express, vol. 9, No. 12, Dec. 1, 2018, pp. 6067-6080.

Zhou H., et al., Age-related changes in choroidal thickness and the volume of vessels and stroma using swept source OCT and fully automated algorithms, Ophthalmology Retina (2019), doi: https://doi.org/10.1016/j.oret.2019.09.012.

Kirby, et al., "Why choroid vessels appear dark in clinical OCT images", Proc. SPIE 10474, Ophthalmic Technologies XXVIII, 1047428 (Feb. 19, 2018); doi: 10.1117/12.2291057.

Maloca, et al., "3D printing of the choroidal vessels and tumours based on optical coherence tomography", Acta Ophthalmologica, vol. 97, doi: 10.1111/aos.13637, 2019, pp. e313-e316.

Kajić, et al., "Automated three-dimensional choroidal vessel segmentation of 3D 1060 nm OCT retinal data", Biomedical Optics Express, vol. 4, No. 1, Jan. 1, 2013, pp. 134-150.

Liu, et al., "Robust deep learning method for choroidal vessel segmentation on swept source optical coherence tomography images" Biomedical Optics Express, vol. 10, No. 4, Apr. 1, 2019, pp. 1601-1612.

Sohrab, et al., "A Pilot Study of Morphometric Analysis of Choroidal Vasculature In Vivo, Using En Face Optical Coherence Tomography", PLOS ONE, vol. 7, Issue 11, e48631, Nov. 2012, www.plosone.org, pp. 1-11.

* cited by examiner

3D ANALYSIS WITH OPTICAL COHERENCE TOMOGRAPHY IMAGES

BACKGROUND OF THE INVENTION

Optical coherence tomography (OCT) is a technique for in-vivo imaging and analysis of various biological tissues (as, for example, two-dimensional slices and/or three-dimensional volumes). Images created from three-dimensional (3D) volumetric OCT data show different appearances/brightness for different components of the imaged tissue. Based on this difference, those components can be segmented out from the images for further analysis and/or visualization. For example, choroidal vasculature has a darker appearance than choroidal stroma in OCT images. Therefore, the choroidal vasculature in OCT images can be segmented out by applying an intensity threshold. However, due to inherent properties of OCT imaging, artifacts in vessel segmentation will emerge if the thresholding is directly applied to the images. Other techniques have thus been developed to segment components of OCT data, but these too suffer from various deficiencies and limitations.

For example, when determining luminal and stromal areas of the choroid by a local binarization method, a special imaging acquisition protocol and averaged line scans are needed to achieve sufficient quality at a depth being analyzed, and to avoid noisy results depending on the type of OCT system utilized. Further, the final threshold is applied manually. Using a choroidal vessel density measurement in 2D projection images lacks depth resolution and can suffer from shadow artifact. Similarly, automated detection of vessel boundaries (even with machine-learning) can be affected by shadow artifacts, and is additionally limited to application in two-dimensional (2D) B-scans only and for larger vessels. Further, the segmented vessel continuity may be poor due the segmentation is repeated for each B-scan in a volume, rather than applied to the volume as a whole. This can thus require each segmented B-scan to be spliced or otherwise pieced together to generate a segmented volume. Other segmentation techniques are only applicable for normal (non-diseased eyes) and suffer errors when retinal structure changes due to diseases. Further, some segmentations are subject to inaccuracies related to the application of noise reduction filters on underlying data.

In short, without noise reduction, averaging of repeated B-scans or along a depth direction is needed to produce data from which the choroidal vasculature can be properly segmented. As a result, the segmentation can be limited in dimension and location. And still further, when applied to 3D data, computation time can be so long as to limit the data that can be analyzed.

Because of these limitations it has not been practical and/or not even possible to present many clinically valuable visualizations and quantifications of choroidal vasculature. For instance, even though a quantitative analysis may be performed on 3D volumetric data or resulting images, the resulting metrics compress the 3D information into a single value. This greatly diminishes the value of, and does not fully utilize, the data. In other instances, the quantifications are taken from OCT data that remains too noisy to perform an accurate analysis, utilize averages taken from many volumes, which can still suffer from noise and also requires increased scanning times (for each iterative volume form which the average is taken), or are limited to relatively small regions of interest (e.g., 1.5 mm under the fovea in single B-scan). Accordingly, medical practitioners have not been able to fully appreciate clinically pertinent information available 3D volumetric OCT data.

BRIEF SUMMARY OF THE INVENTION

According to the present disclosure, a three dimensional (3D) quantification method comprises: acquiring 3D optical coherence tomography (OCT) volumetric data of an object of a subject, the volumetric data being from one scan of the object; pre-processing the volumetric data, thereby producing pre-processed data; segmenting a physiological component of the object from the pre-processed data, thereby producing 3D segmented data; determining a two-dimensional metric of the volumetric data by analyzing the segmented data; and generating a visualization of the two-dimensional metric.

In various embodiments of the above example, segmenting the physiological component comprises: performing a first segmentation technique on the pre-processed data, thereby producing first segmented data, the first segmentation technique being configured to segment the physiological component from the pre-processed data; performing a second segmentation technique on the pre-processed data, thereby producing second segmented data, the second segmentation technique being configured to segment the physiological component from the pre-processed data; and producing the 3D segmented data by combining the first segmented data and second segmented data, wherein the first segmentation technique is different than the second segmentation technique; the pre-processing includes de-noising the volumetric data; the object is a retina, and the physiological component is choroidal vasculature; the metric is a spatial volume, diameter, length, or volumetric ratio, of the vasculature within the object; the visualization is a two-dimensional map of the metric in which a pixel intensity of the map indicates a value of the metric at the location of the object corresponding to the pixel; a pixel color of the map indicates a trend of the metric value at the location of the object corresponding to the pixel; the trend is between the value of the metric of the acquired volumetric data and a corresponding value of the metric from an earlier scan of the object of the subject; the trend is between the value of the metric of the acquired volumetric data and a corresponding value of the metric from the object of a different subject; determining the trend comprises: registering the acquired volumetric data to comparison data; and determining a change between the value of the metric of the acquired volumetric data and a corresponding value of the metric of the comparison data; portions of the acquired volumetric data and the comparison data used for registration are different than portions of the acquired volumetric data and the comparison data used for determining the metrics; the object is a retina, and the physiological component is choroidal vasculature, and the metric is a spatial volume of the vasculature within the object; pre-processing the volumetric data comprises: performing a first pre-processing on the volumetric data, thereby producing first pre-processed data; and performing a second pre-processing on the volumetric data, thereby producing second pre-processed data, and segmenting the physiological component comprises: performing a first segmentation technique on the first pre-processed data, thereby producing first segmented data, performing a second segmentation technique on the second pre-processed data, thereby producing second segmented data; and producing the 3D segmented data by combining the first segmented data and the second segmented data; the first segmentation technique and the second segmentation technique are the same; the first segmentation technique and the second segmentation technique are different; pre-processing the volumetric data comprises: performing a first pre-processing on a first portion of the volumetric data, thereby producing first pre-processed data; and performing a second pre-processing on a second portion of the volumetric data, thereby producing second pre-processed data, segmenting the physiological component comprises: segmenting the physiological component from the first pre-processed data, thereby producing first segmented data; segmenting the physiological component from the second pre-processed data, thereby producing second segmented data; and producing the 3D segmented data by combining the first segmented data and the second segmented data, and the first portion and the second portion do not fully overlap; segmenting the physiological component comprises applying a 3D segmentation technique to the pre-processed data; the pre-processing comprises applying a local Laplacian filter to the volumetric data that corresponds to a desired depth range and region of interest; the pre-processing comprises applying a shadow reduction technique to the volumetric data; the method further comprises aggregating the metric within a region of interest, wherein the visualization is a graph of the aggregated metric; and/or the method further comprises generating a visualization of the 3D segmented data.

DETAILED DESCRIPTION OF THE INVENTION

The present disclosure relates to clinically valuable analyses and visualizations of three-dimensional (3D) volumetric OCT data that was not previously practical and/or possible with known technologies. Such analyses and visualizations may improve a medical practitioner's ability to diagnose disease, monitor, and manage treatment. Briefly, the analysis is performed on, and the visualizations are created by, segmenting OCT data for a component of interest (e.g., choroidal vasculature) in three dimensions following a series of pre-processing techniques. The segmentation can be applied to the data following pre-processing, and then combined to produce a final full 3D segmentation of the desired component. Post-processing, such as a smoothing technique, may be then applied to the segmented component. While choroidal vasculature of OCT data is particularly discussed herein, the disclosure is not to be so limited.

Figure 1:
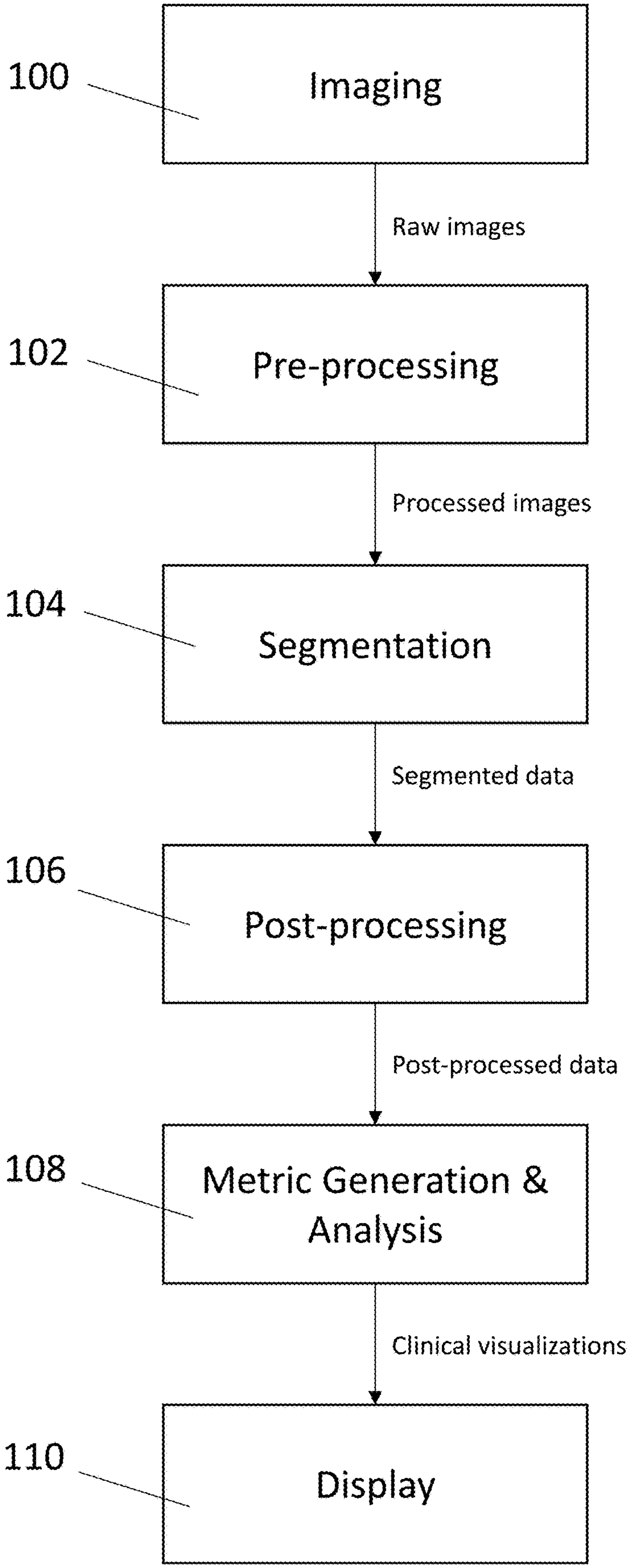
FIG. 1 illustrates a flow chart of an example method according to the present disclosure.

An example method for producing clinically valuable analyses and visualizations according to the present disclosure is illustrated in FIG. 1. As seen therein, 3D volumetric OCT data is acquired and corresponding raw images (hereinafter the terms "images" and "data" are used interchangeably as the images are the representations of underlying data in a graphical form) are generated by imaging 100 a subject's eye. Following imaging, individual 2D images (or many 2D images collectively as a 3D volume) are pre-processed 102. The pre-processing 102 may, for example, address speckle and other noise in the data and images by applying a deep-learning based noise reduction technique, such as that described in U.S. patent application Ser. No. 16/797,848, filed Feb. 21, 2020 and titled "Image Quality Improvement Methods for Optical Coherence Tomography," the entirety of which is herein incorporated by reference. Further, shadow and projection artifacts may be reduced by applying image-processing and/or deep-learning techniques, such as that described in U.S. patent application Ser. No. 16/574,453, filed Sep. 28, 2019 and titled "3D Shadow Reduction Signal Processing Method for Optical Coherence Tomography (OCT) Images," the entirety of which is herein incorporated by reference. Of course, other de-noising techniques may be applied.

Intensity attenuation along the depth dimension may be addressed by applying a intensity compensation and contrast enhancement techniques. Such techniques may be locally applied, for example, as a local Laplacian filter at desired depths and regions of interest (in either 2D or 3D). In addition to, or alternatively, a contrast-limited adaptive histogram equalization (CLAHE) technique, may be applied to enhance contrast. Of course, other contrast enhancement techniques (applied locally or globally), and/or other pre-processing techniques may be applied.

The pre-processing 102 may be applied to entire images or volumes, or only selected regions of interest. As a result, for each raw image or volume input to the pre-processing 102, multiple pre-processed images may be produced. Put another way, individual B-scans or C-scans taken from raw volumetric OCT data may be subject to different pre-processing techniques to produce multiple pre-processed images. Following pre-processing 102, the pre-processed images (or data underlying the images) are segmented 104 for a desired component in the images/data, such as choroidal vasculature. The segmentation process 104 may utilize one or more different techniques, where each applied segmentation technique may individually be relatively simple and fast to perform, and have different strengths and weaknesses.

For example, some segmentation techniques may utilize different thresholding levels, and/or may be based on analysis from different views (e.g., a B-scan or C-scan). More particularly, performing segmentation on C-scans can improve continuity of vessels relative to segmentation performed on B-scans because each C-scan image contains information in the entire field of view of volume. This further allows for segmentation of smaller vessels relative to segmentation on B-scans, and makes manual validation of the segmentation easier for a user. However, segmentation on C-scans may be dependent on the accuracy of a preceding Bruch's membrane segmentation used to flatten the volumetric data.

In view of the above, the different segmentation techniques can be selectively applied to one or more of the pre-processed images. Further, as suggested above, global segmentation on an entire OCT volume has not been practically possible due to noise and attenuation (e.g., causing artifacts). However, following application of the above-described pre-processing, the segmentation techniques may also be applied to entire OCT volumes, rather than individual B-scans or C-scans from the volumes. In any case, each of the segmentation techniques segments the desired component in the pre-processed images/data. Segmentation applied to entire volumes can further improve connectivity of the segmentation, since individual segmentations need not be pieced together, although such segmentations may be less sensitive to local areas of the volume with relatively low contrast, but this can be mitigated by depth compensation and contrast enhancement techniques described above.

In one example embodiment, each segmentation technique may be applied to images/data having been separately pre-processed. In another embodiment, segmentation techniques may be selectively applied to images/data corresponding to different regions of interest. For example, a first two pre-processed images may be segmented according to a first segmentation technique, while a second two pre-processed images may be segmented according a second segmentation technique. In another embodiment, after 3D volumetric OCT data has been pre-processed according to any number of techniques, a local thresholding segmentation technique is applied on B-scan images taken from the pre-processed 3D volumetric OCT data to generate a first determination of choroidal vasculature, a local thresholding technique is applied on C-scan images taken from the pre-processed 3D volumetric OCT data to generate a second determination of choroidal vasculature, and a global thresholding technique is applied to the entirety of the pre-processed 3D volumetric data to generate a third determination of choroidal vasculature.

Regardless of the number of pre-processing and segmentation techniques applied, the segmentations are then combined to produce a composite segmented image or data, which is free from artifacts and of sufficient quality for both processing to determine different quantitative metrics as part of an analysis 108, and visualization of the segmentation and/or the metrics 110. The composite image may thus include all of the pre-processing and segmentation techniques, and may be combined according to any method such as union, intersection, weighting, voting, and the like. Following segmentation 104, the segmented image or data may also be further post-processed, for example, for smoothing.

Figure 2:
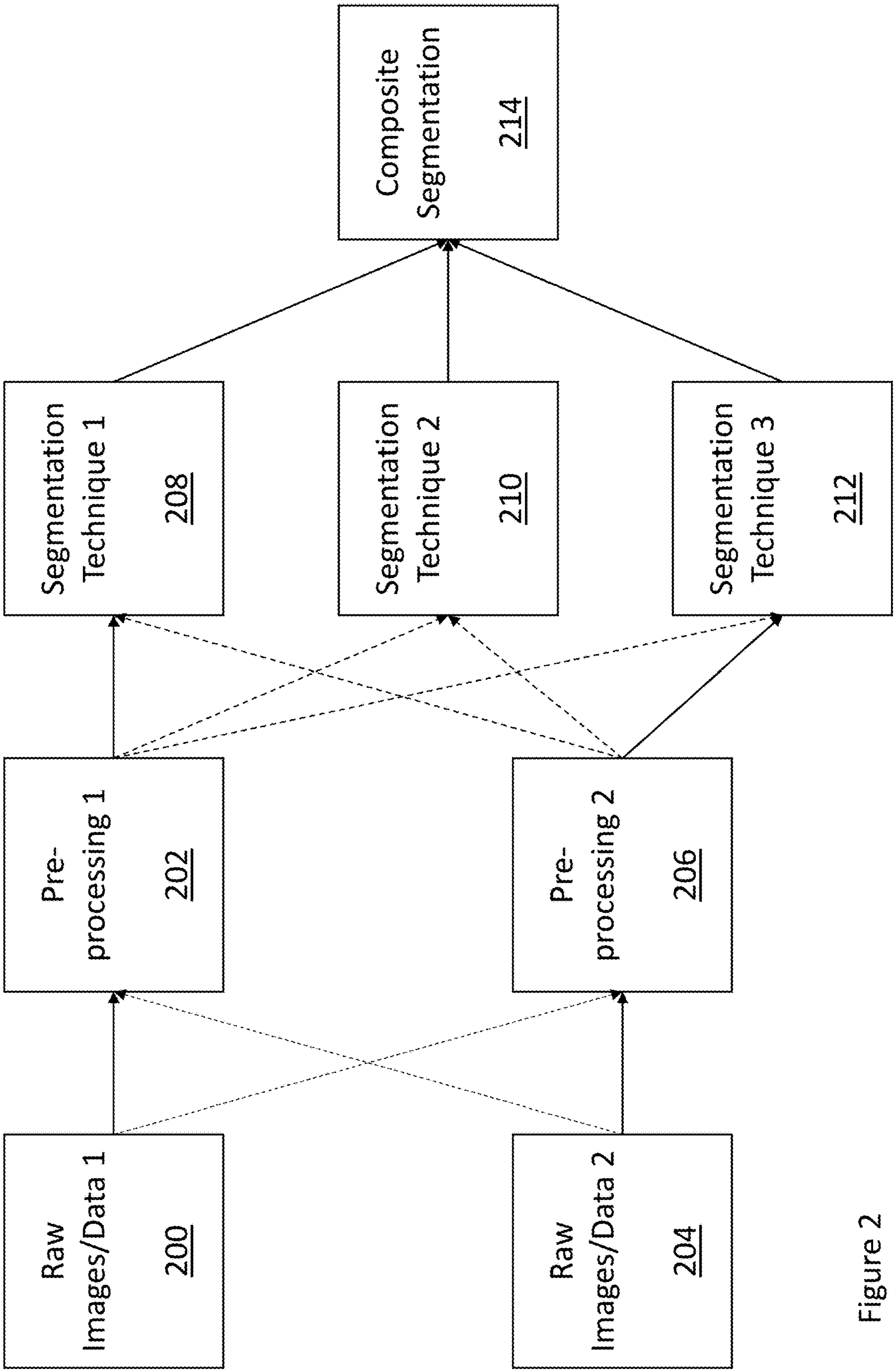
FIG. 2 illustrates an example application of pre-processing and segmentation according to the present disclosure.

The above combination of pre-processing and segmentation is illustrated schematically with respect to FIG. 2. The example therein utilizes two sub-sets of raw images and data, each from a common 3D volumetric OCT data set. The subsets of images/data may be separated according to region of interest, by view (e.g., B-scans and C-scans), and the like. According to the example of FIG. 2, the first subset 200 is subject to a first pre-processing 202, while the second subset 204 is subject to a second pre-processing 206. In other embodiments (indicated by the dashed lines), each subset 200, 204 may be subject to any of the available pre-processings 202, 206. The data associated with the first subset 200 thus results in at least one pre-processed data subset, while the data associated with the second subset 204 thus results in at least two pre-processed data subsets. Following pre-processing, each resulting data set is then similarly segmented by any available segmentation technique (three shown for example). As illustrated, the results of each pre-processing are segmented separately by different segmentation techniques 208, 210, 212; however, in other embodiments (indicated by the dashed lines), one or more of the segmentation techniques 208, 210, 212 may be applied to any of the pre-processed images/data. Finally, the outputs of each segmentation technique 208, 210, 212 are combined 214 as discussed above to produce a composite segmentation. In view of the above, common raw images and data may be subject to different pre-processing and/or segmentation techniques as part of the method for producing a single composite segmentation of the 3D volumetric OCT data from which the raw images and data originated.

Figure 3:
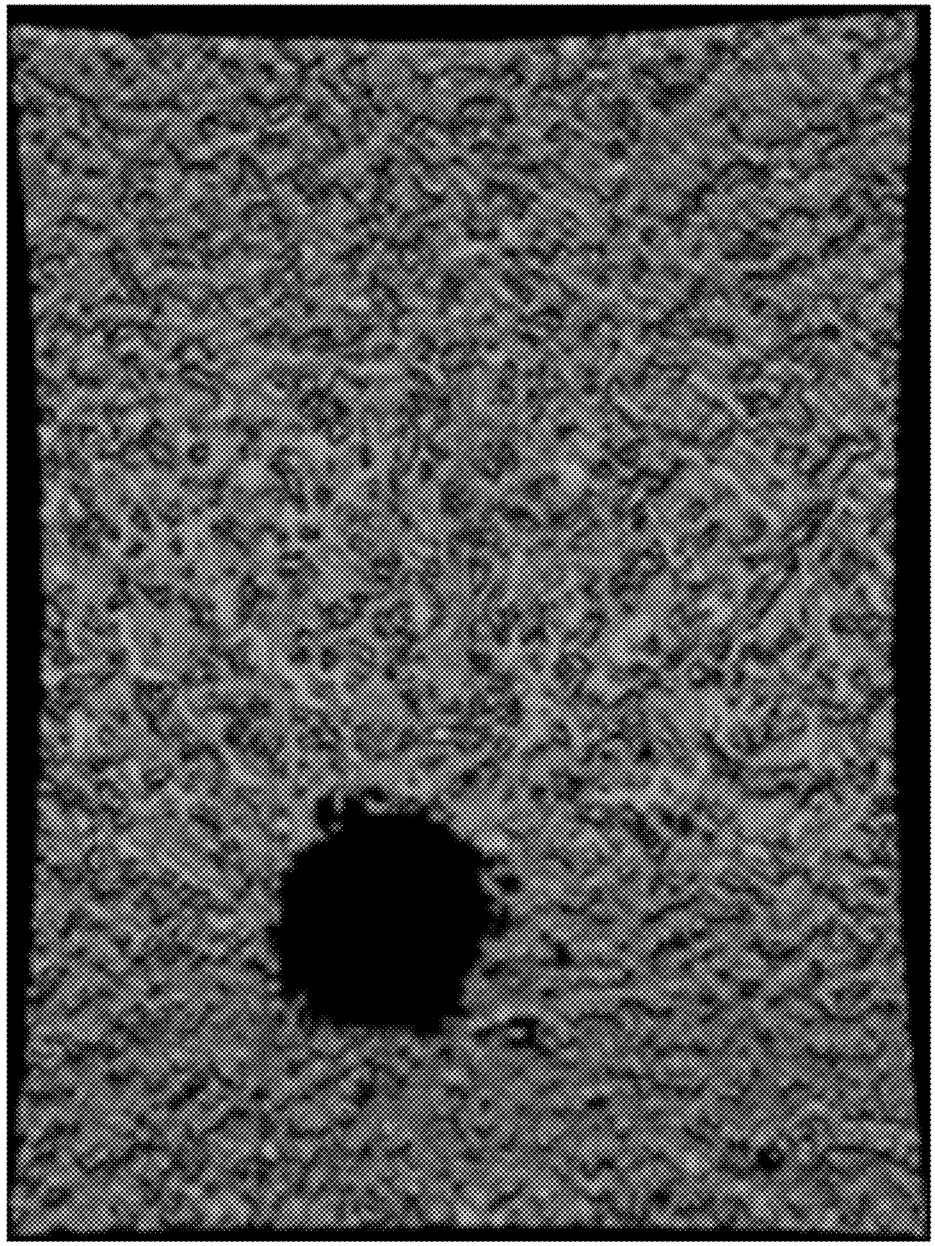
FIG. 3 illustrates an example composite image generated according to the present disclosure.

As noted above, utilizing the plurality of pre-processing and segmentation techniques to produce a composite result, rather than performing a single complex pre-processing and segmentation reduces the total pre-processing and segmentation time and computational power. Nevertheless, the same quality may be achieved, and the segmentation can be applied to, entire 3D volumes. The resulting segmentation can thus be free from noise and shadow artifacts and be of sufficient quality for visualization and quantification (discussed below). An example composite image according to the above is illustrated in FIG. 3. Therein, choroidal vasculature segmented out of 3D volumetric OCT data is rendered in a 3D view.

Referring back to FIG. 1, the composite image or volume may then be processed to generate and analyze many quantifiable metrics 108 based on the entire volumetric OCT data, rather than two-dimensional data of B-scans previously used to for quantitative analysis of the volume. Because these metrics are generated from the above-described pre-processed and segmented OCT data, the metrics may significantly more accurate than those derived from OCT data according to traditional techniques. Further, the metrics (and the segmented visualization such as that in FIG. 3 and any visualizations generated from the metrics) may be determined with respect to relatively large areas (e.g., greater than 1.5 mm of a single B-scan) over multiple 2D images of a volume or even whole volumes, and from a single OCT volume (as captured from a single scan, rather than an average of multiple scans).

For example, within a 3D volume, the spatial volume (and relatedly, density being a proportion of the entire volume in a given region that is vasculature or like segmented component), diameter, length, volumetric ratio (also referred to as an index), and the like, of vasculature can be identified by comparing data segmented out in the composite segmented image relative to the un-segmented data. For example, counting the number of pixels segmented out may provide an indication of the amount of vasculature (e.g., volume or density) within a region of interest. By projecting those metrics alone one dimension (e.g., taking a maximum, minimum, mean, sum, or the like) such as depth, then a volume map, diameter map, index map, and the like can be generated. Such a map can visually show the quantified value of the metric for each location on the retina. Further, it is possible to identify the total volume, representative index, or the like by aggregating those metrics in a single dimension (e.g., over the entire map). Quantifying such metrics over large areas and from a single OCT volume permits previously unavailable comparison of volumetric OCT data between subjects, or of an individual subject over time.

The metrics may also be comparative. For example, a comparative metric may be based on metrics of OCT volumes obtained from a single subject at different times, from different eyes (e.g., right and left eyes of a single individual), from multiple subjects (e.g., between an individual collective individuals representative of a population), or from different regions of interest of the same eye (e.g., different layers). These comparisons may be made by determining the metric for each element of the comparison and then performing any statistical comparison technique. For example, the comparative metric may be a ratio of the comparative data, a difference between the comparative data, an average of the comparative data, a sum of the comparative data, and/or the like. The comparisons may be made generally for a total volumetric data or on a location-by-location basis (e.g., at each pixel location of a comparative map).

When comparing metrics from common regions of interest, the compared elements (different data sets, images, volumes, metrics, and the like) are preferably registered to each other so that like comparisons can be made. In other words, the registration permits corresponding portions of each element to be compared. In some instances, for example when comparing changes in choroidal vasculature, the registration may not be made based on the vasculature itself because the vasculature is not necessarily the same in each element (e.g., due to treatments over the time periods being compared). Put more generally, registration is preferably not performed based on information that may be different between the elements or that is used in the metrics being compared. In view of this, in some embodiments registration may be performed based on en face images generated from raw (e.g., not pre-processed) OCT volumes of each compared element. These en face images may be generated be summation, averaging, or the like of intensities along each A-line in the region being used for registration. En face images are helpful in registration because retinal vessels can cast shadows, thus on OCT en face images, the darker retinal vasculature that stays relatively stable can serve as a landmark. Further, by nature, any metrics, choroidal vasculature images, or like images generated from an OCT volume are co-registered with the en face image because they come from the same volume. For example, superficial vessels in a first volume may be registered to superficial vessels in a second volume, and choroidal vessels (or metrics of the choroidal vessels) in the first volume may be compared to choroidal vessels in the second volume.

Visualizations of these metrics may then be produced and displayed 110 or stored for later viewing. That is, the techniques described herein are capable of producing not only visualizations of the segmented components of volumetric OCT data (e.g., choroidal vasculature) but also visualizations (e.g., maps and graphs) of quantified metrics related to that segmented component. Visualization of these quantified metrics further simplifies the above-noted comparisons. Such visualizations may be 2D representations of the metrics representing 3D volumetric information, and/or representations of the comparative metrics representing changes and/or differences between two or more OCT volumes. Considering the above-mentioned metrics, the visualizations may be, for example, a choroidal vessel index map, a choroidal thickness map, or a vessel volume map, and/or comparisons of each.

Information may be encoded in the visualizations in various forms. For example, an intensity of each pixel of the visualization may indicate a value of the metric at the location corresponding to the pixel, while color may indicate a trend of the value (or utilize intensity for the trend and color for the value). Still other embodiments may use different color channels to identify different metric information (e.g., a different color for each metric, with intensity representing a trend or value for that metric). Still other embodiments may utilize various forms of hue, saturation, and value (HSV) and/or hue, saturation, and light (HSL) encoding. Still other embodiments may utilize transparency to encode additional information. Example visualizations are illustrated in FIGS. 4-7.

Figure 4:
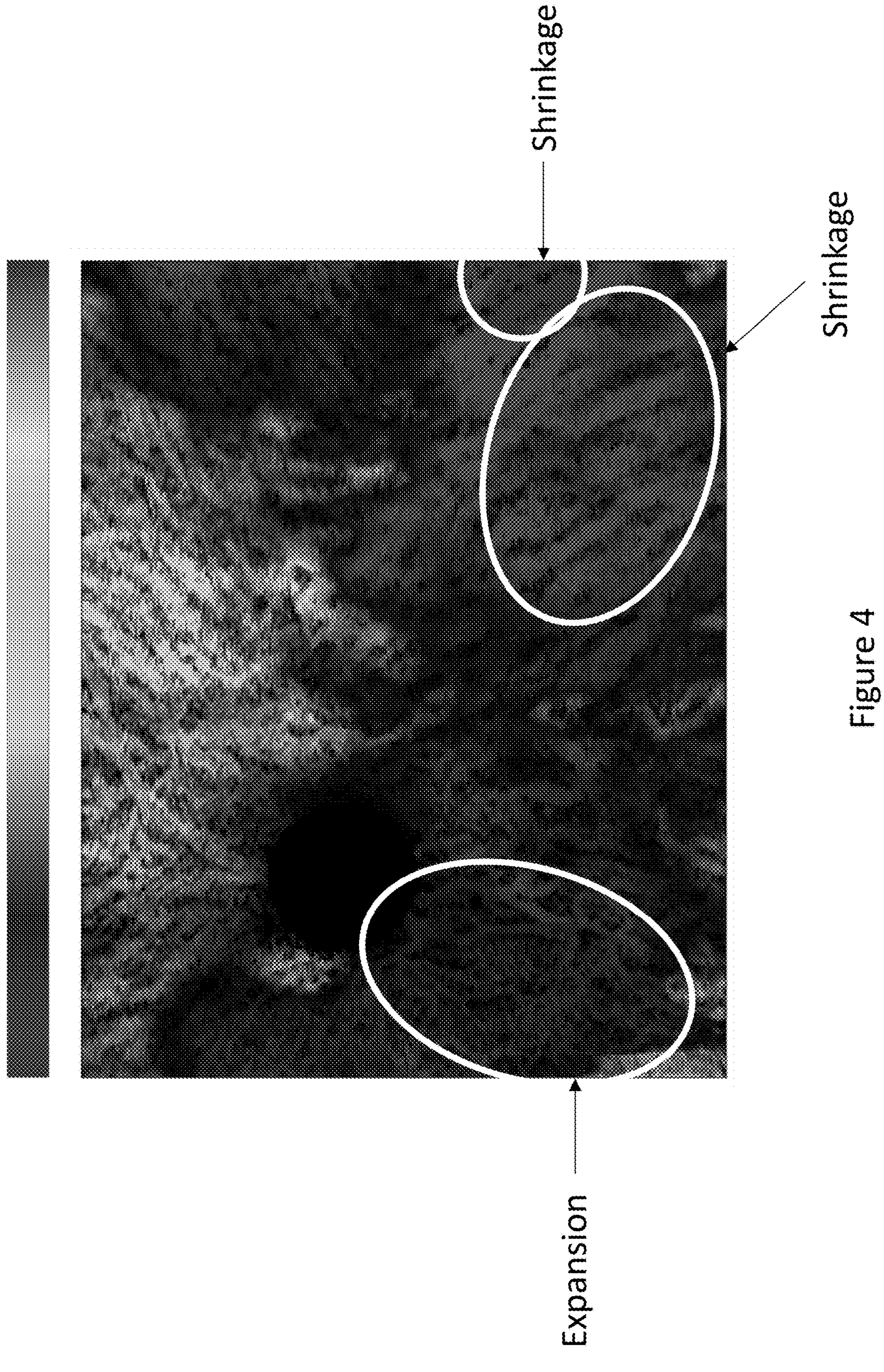
FIG. 4 illustrates an example visualization according to the present disclosure.

FIG. 4 illustrates a first example visualization according to the present disclosure. The visualization of FIG. 4 is a 2D image of choroidal vasculature, where the intensity of each pixel corresponds to a metric and color indicates a local trend of the metric as compared with a previous scan. For example, the intensity of each pixel may correspond to a vessel volume, vessel length, vessel thickness, or like measurement of the 3D volumetric data. The color may then illustrate a change in each pixel as compared with a previous metric measurement from a previously captured 3D volumetric data. For example, a red color may be used to indicate expansion of the vasculature measurement since the previous measurement, while a purple color may indicate shrinkage of the vasculature. Blues and greens may indicate a relatively consistent measurement (i.e., little or no change). As distinct colors are not shown in the black-and-white image of FIG. 4, example regions corresponding to shrinkage (e.g., identified as purples) and expansion (e.g., identified as reds) are expressly identified for reference. The comparison to previous measurements may be taken as a simple difference, a change relative to an average of a plurality of measurements, a standard deviation, and/or like statistical calculation. Of course, the correlation between colors and the change may be set according to other schemes.

Figure 5A:
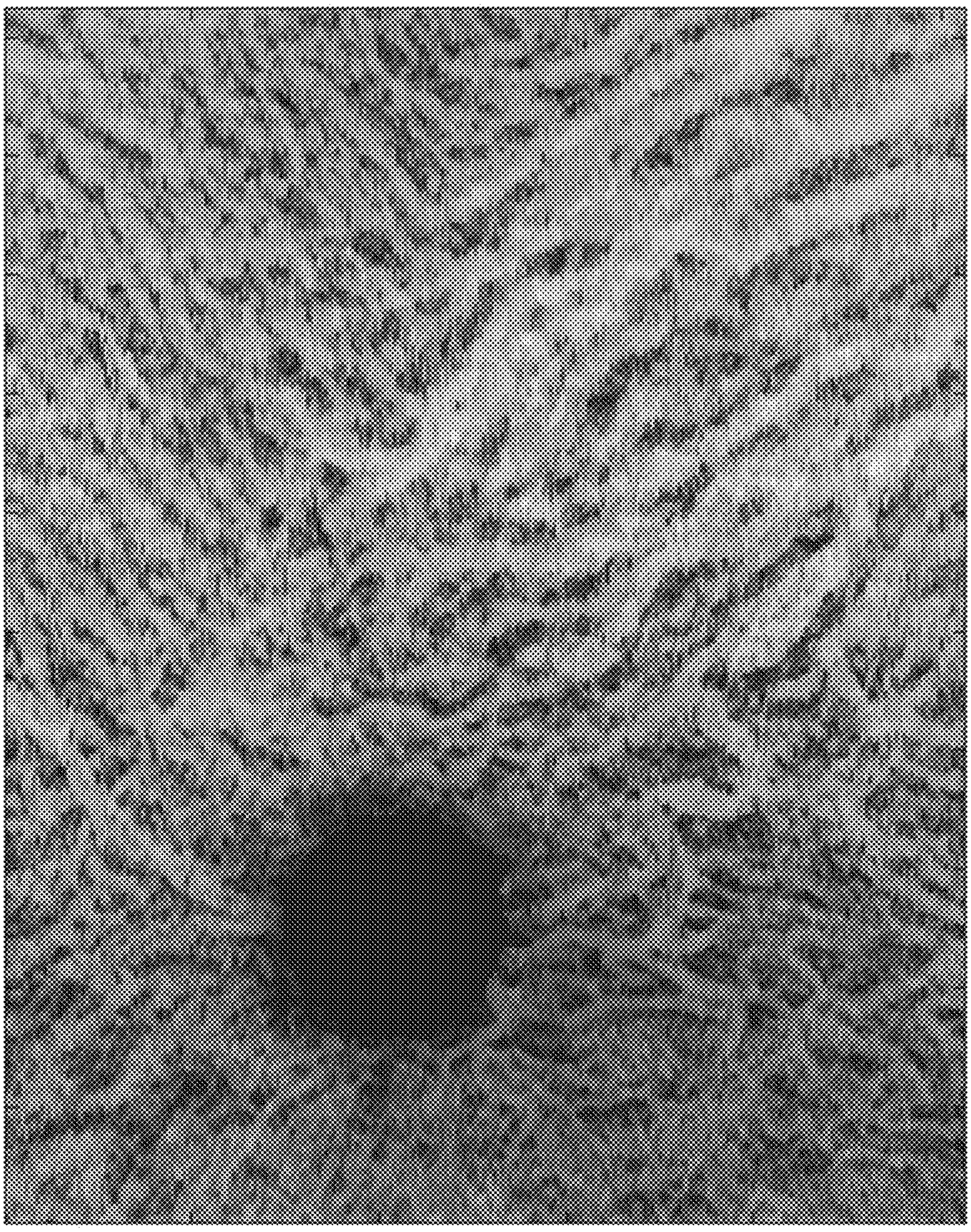
FIGS. 5A and 5B illustrate example choroidal vessel 2D volume maps as example visualizations according to the present disclosure.
Figure 5B:
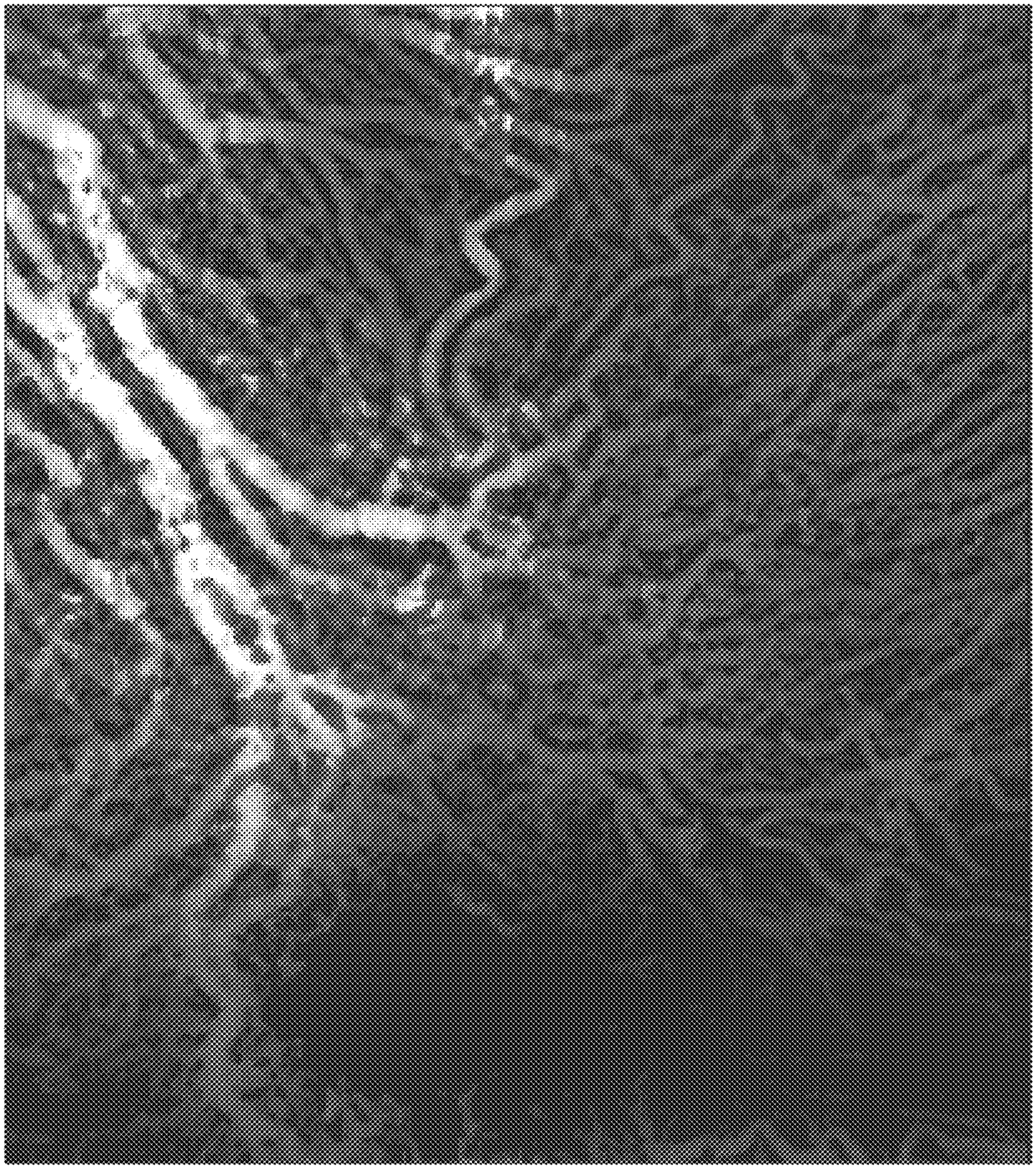

FIGS. 5A and 5B each illustrate example choroidal vessel 2D volume maps as an example visualization according to the present disclosure. The choroidal vasculature volume of a 3D volumetric data set may be determined as the number of pixels corresponding to choroidal vasculature for each A-line of a 3D volumetric data multiplied by the resolution of each pixel. Where the aggregation occurs over depth, each pixel of the volume map corresponds to one A-line of the 3D volumetric data set. As with the example of FIG. 4, the intensity of each pixel in the volume map corresponds to the vessel volume at the corresponding location, while the color corresponds to a local trend in that volume as compared to a previous scan. Similarly, comparing the number of segmented pixels to the total number of pixels in the choroid (or other region) can provide a quantification of the vasculature (or other component) density over the region. Generally, volume and density may increase or decrease together.

As suggested above, metrics used to generate the 2D visualization maps may be further aggregated over regions of interest for additional analysis. For example, the metric values and/or pixel intensities may be aggregated for regions corresponding to the fovea (having a 1 mm radius), parafovea (superior, nasal, inferior, tempo) (having a 1-3 mm radius from the fovea center), perifovea (superior, nasal, inferior, tempo) (having a 3-5 mm radius from the fovea center), and/or the like. The aggregation may be determined by any statistical calculation, such as a summation, standard deviation, and the like. If the aggregated numbers are collected at different points in time, a trend analysis can be performed and a corresponding trend visualization generated. The aggregated numbers can also be compared between patients or to a normative value(s).

Figure 6:
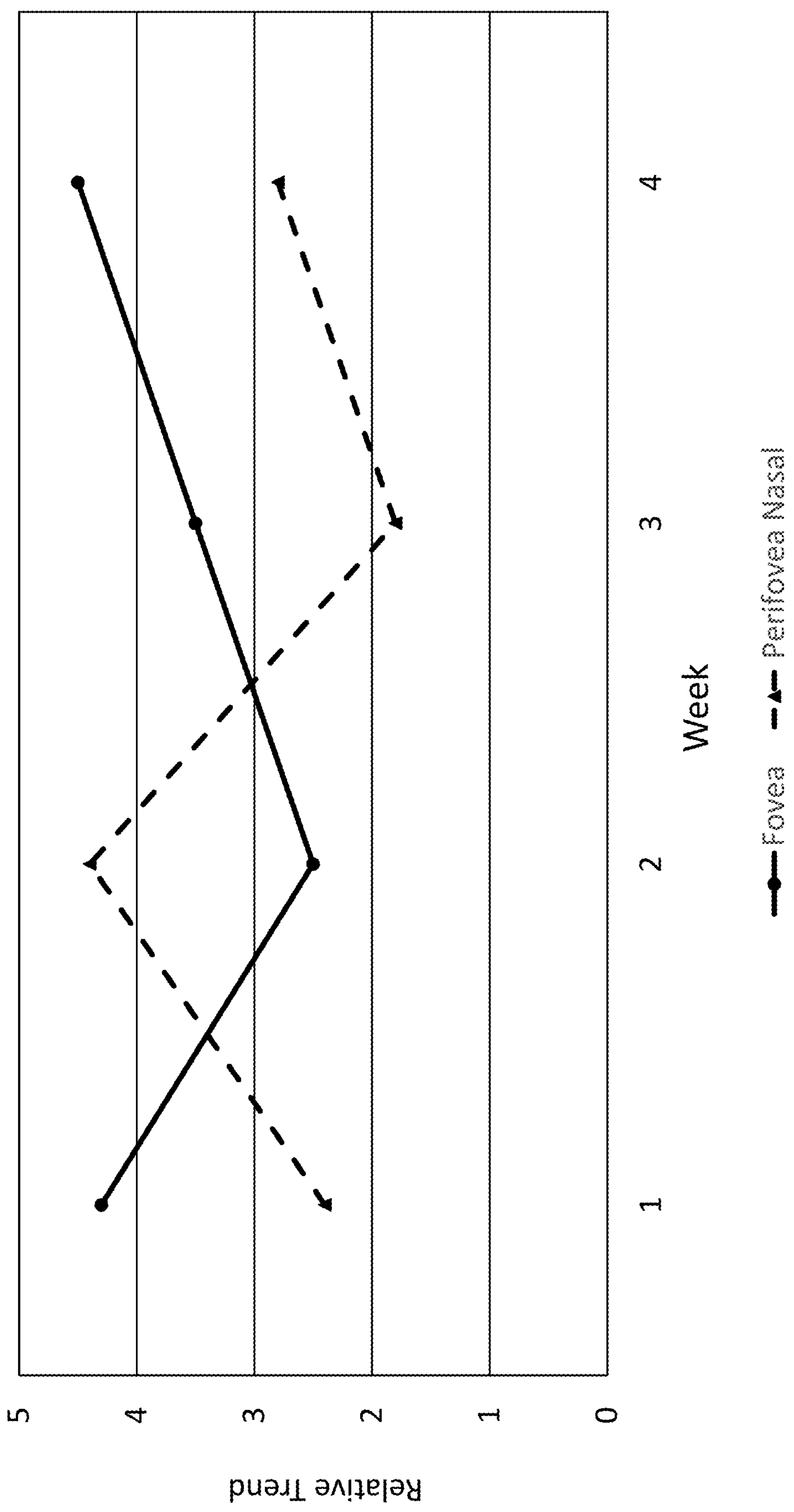
FIG. 6 illustrates a choroidal volume trend as an example visualization according to the present disclosure.

An example visualization of a choroidal volume trend for the fovea and perifovea nasal is illustrated in FIG. 6. As can be seen therein, choroidal volume was aggregated in each of the fovea and the perifovea nasal regions each week for a period of four weeks. The visualization makes it clear to see that the subject had an increase in vasculature volume in the perifovea nasal between weeks one and two, and a corresponding decrease in volume in the fovea over the same time. However, as vasculature volume in the fovea began to increase in week three, the volume in the perifovea nasal decreased below its original value. The volume in each region increased between weeks three and four.

Figure 7:
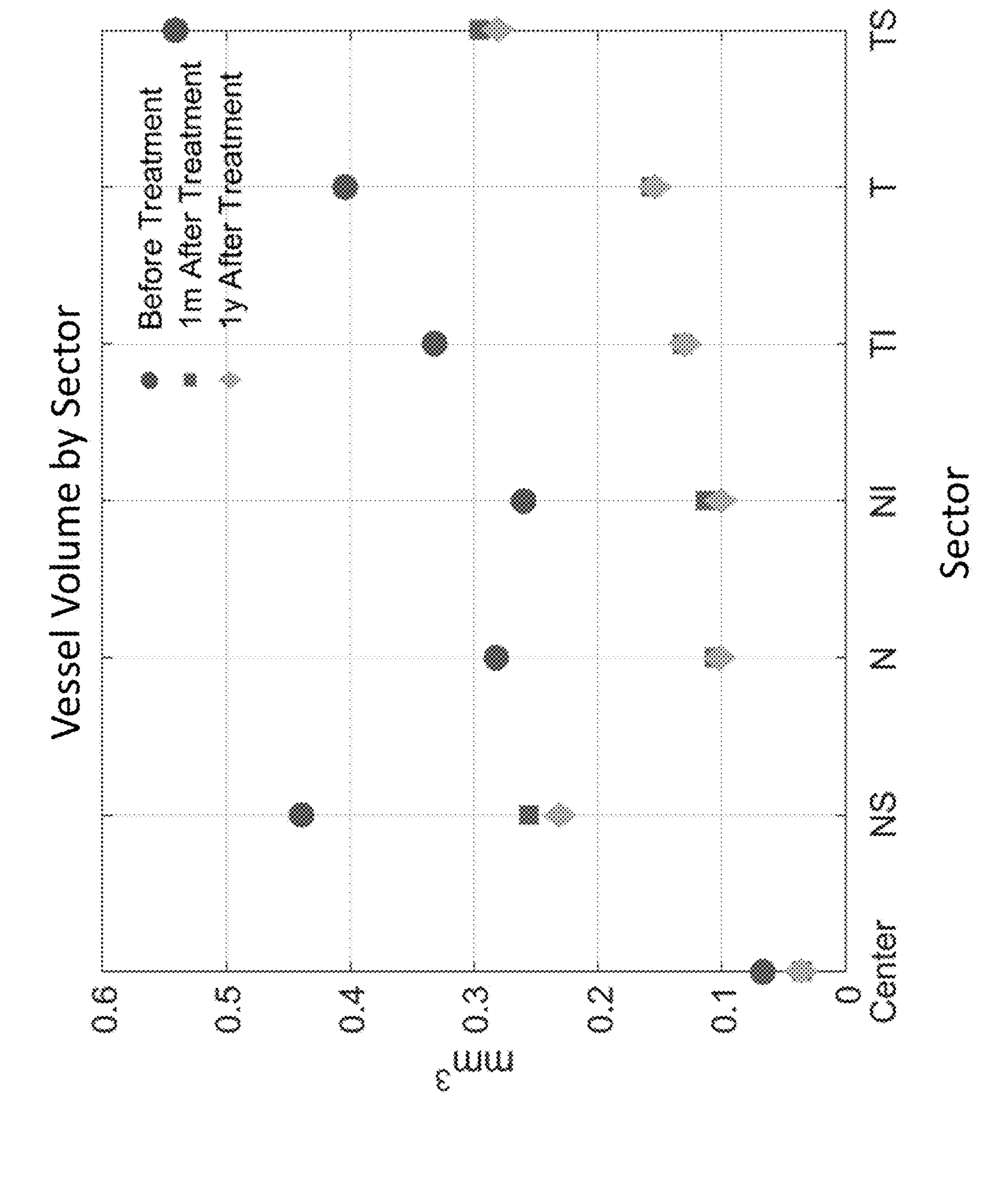
FIG. 7 illustrates vessel volume as an example visualization according to the present disclosure.

Another example visualization is illustrated in FIG. 7. Therein, the total volume of the choroidal vasculature is shown for different sectors of the choroid: fovea (center), nasal-superior (NS), nasal (N), nasal-inferior (NI), temp-inferior (TI), tempo (T), and tempo-superior (TS). The total volumes may be determined by summing the total number of choroidal vasculature pixels within each sector. Based on a resolution of the 3D data, the total number of pixels may then be converted to a physical size (such as cubic millimeters). According to the visualization of FIG. 7, the volumes are shown prior to a treatment of the patient, one month following treatment, and one year following treatment. As can be seen, the volume of the vasculature greatly decreases in each sector following treatment.

Of course, similar 2D map and trend visualizations may be generated for different metrics. For example, a vessel thickness map and trend visualization may be generated by determining a total number of choroidal vasculature pixels for each A-line of a 3D volumetric data set; or a non-vessel index map and trend visualization may be generated by determining a total number of non-vessel pixels within a region (such as the choroid).

The above-described aspects are envisioned to be implemented via hardware and/or software by a processor. A "processor" may be any, or part of any, electrical circuit comprised of any number of electrical components, including, for example, resistors, transistors, capacitors, inductors, and the like. The circuit may be of any form, including, for example, an integrated circuit, a set of integrated circuits, a microcontroller, a microprocessor, a collection of discrete electronic components on a printed circuit board (PCB) or the like. The processor may be able to execute software instructions stored in some form of memory, either volatile or non-volatile, such as random access memories, flash memories, digital hard disks, and the like. The processor may be integrated with that of an OCT or like imaging system but may also stand alone or be part of a computer used for operations other than processing image data.

What is claimed is:

1. A three dimensional (3D) quantification method, comprising:

acquiring 3D optical coherence tomography (OCT) volumetric data of an object of a subject, the volumetric data being from one scan of the object;

performing a plurality of different pre-processing techniques on the volumetric data, thereby producing a plurality of different pre-processed data;

segmenting a physiological component of the object from the volumetric data by applying a plurality of different segmentation techniques to each of the plurality of different pre-processed data, thereby producing a plurality of different segmented data;

combining the plurality of different segmented data, thereby producing 3D composite segmented data;

determining a quantifiable metric of the volumetric data by analyzing the 3D composite segmented data;

registering the 3D composite segmented data to comparison data based on a first portion of the 3D composite segmented data and a corresponding first portion of the comparison data;

determining a trend of the metric by determining a change between a value of the metric of the 3D composite segmented data at a second portion of the 3D composite segmented data and a value of the metric of the comparison data at a corresponding second portion of the comparison data; and generating a two-dimensional map of the metric, the map indicating the determined trend of the metric value, wherein the first portions of the 3D composite segmented data and comparison data are different than the second portions of 3D composite segmented data and comparison data.

2. The method of claim 1, wherein the plurality of pre-processing techniques comprise de-noising the volumetric data.

3. The method of claim 1, wherein the object is a retina, and the physiological component is choroidal vasculature.

4. The method of claim 3, wherein the metric is a spatial volume, diameter, length, or volumetric ratio, of the vasculature within the object.

5. The method of claim 1, wherein a pixel intensity of the map indicates the value of the metric at a location of the object corresponding to the pixel.

6. The method of claim 5, wherein a pixel color of the map indicates the trend of the metric value at the location of the object corresponding to the pixel.

7. The method of claim 6, wherein the trend is between the value of the metric of the acquired volumetric data and a corresponding value of the metric from an earlier scan of the object of the subject.

8. The method of claim 6, wherein the trend is between the value of the metric of the acquired volumetric data and a corresponding value of the metric from the object of a different subject.

9. The method of claim 5, wherein:

the object is a retina, and the physiological component is choroidal vasculature, and the metric is a spatial volume of the vasculature within the object.

10. The method of claim 1, wherein the plurality of segmentation techniques comprise a 3D segmentation technique.

11. The method of claim 1, wherein the plurality of pre-processing techniques comprise applying a local Laplacian filter to the volumetric data that corresponds to a desired depth range and region of interest.

12. The method of claim 1, wherein the plurality of pre-processing techniques comprise applying a shadow reduction technique to the volumetric data.

13. The method of claim 1, further comprising aggregating the metric within a region of interest, wherein the visualization is a graph of the aggregated metric.

14. The method of claim 1, further comprising generating a visualization of the 3D composite segmented data.

15. The method of claim 1, wherein the comparison data is acquired volumetric data from an earlier scan of the object of the subject.

16. The method of claim 1, wherein the comparison data is acquired volumetric data from the object of a different subject.

* * * * *